US00PP33718P2

(12) United States Plant Patent
Caster et al.

(10) Patent No.: US PP33,718 P2
(45) Date of Patent: Dec. 7, 2021

(54) BLUEBERRY PLANT NAMED 'DRISBLUETWENTYFIVE'

(50) Latin Name: ***Vaccinium corymbosum* L.**
Varietal Denomination: DrisBlueTwentyFive

(71) Applicant: Driscoll's, Inc., Watsonville, CA (US)

(72) Inventors: Brian K. Caster, Watsonville, CA (US); Jennifer K. Izzo, Watsonville, CA (US); Bruce D. Mowrey, Watsonville, CA (US); Marta C. Baptista, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/179,260

(22) Filed: Feb. 18, 2021

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
CPC ... A01H 5/08; A01H 5/00; A01H 5/02; A01H 6/36; A01H 6/368
See application file for complete search history.

(56) References Cited

U.S. PATENT DOCUMENTS

PP6,699 P 3/1989 Wood
PP11,807 P2 3/2001 Lyrene
PP12,783 P2 7/2002 Lyrene
PP15,146 P3 9/2004 Hancock
PP19,503 P3 11/2008 Lyrene
PP20,436 P2 10/2009 Caster et al.
PP20,449 P2 11/2009 Caster et al.
PP20,488 P2 11/2009 Caster et al.
PP24,407 P3 4/2014 Caster et al.
PP24,489 P3 5/2014 Lyrene et al.
PP24,568 P3 6/2014 Caster et al.
PP24,569 P3 6/2014 Caster et al.
PP24,605 P3 7/2014 Caster et al.
PP26,287 P3 1/2016 Caster et al.
PP26,451 P3 3/2016 Rodriguez et al.
PP26,537 P3 3/2016 Caster et al.
PP26,643 P3 4/2016 Caster et al.
PP26,748 P3 5/2016 Rodriguez et al.
PP27,622 P3 1/2017 Caster et al.
PP28,933 P2 2/2018 Caster et al.
PP31,649 P2 4/2020 Caster et al.
PP31,650 P2 4/2020 Caster et al.
PP31,685 P2 4/2020 Mowrey et al.
PP31,698 P2 4/2020 Mowrey et al.
PP32,267 P2 10/2020 Caster et al.
PP32,744 P3 1/2021 Caster et al.
PP32,876 P2 3/2021 Mowrey et al.

*Primary Examiner* — June Hwu

(74) *Attorney, Agent, or Firm* — Morrison & Foerster LLP

(57) ABSTRACT

A new and distinct variety of blueberry plant named 'DrisBlueTwentyFive', particularly selected for its sweet flavor, large fruit size, improved post-harvest storage qualities, and early ripening, is disclosed.

7 Drawing Sheets

Latin name: Botanical classification: *Vaccinium corymbosum* L.

Varietal denomination: The varietal denomination of the claimed variety of blueberry plant is 'DrisBlueTwentyFive'.

BACKGROUND OF THE INVENTION

Blueberry plants are perennial flowering plants with indigo-colored berries from the section *Cyanococcus* within the genus *Vaccinium*. Many commercially sold species with English common names, including blueberry, are currently classified in section *Cyanococcus* of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L.), which has been denominated as 'DrisBlueTwentyFive'.

Blueberry plant variety 'DrisBlueTwentyFive' originated from a cross between the proprietary female parent blueberry plant '90E 2' (unpatented) and the proprietary male parent blueberry plant '10E 1' (unpatented). Progeny plants from this cross of '90E 2' x '10E 1', including 'DrisBlueTwentyFive' were evaluated in Santa Cruz County, Calif., and 'DrisBlueTwentyFive' was specifically identified and selected in July of 2011. 'DrisBlueTwentyFive' was later asexually propagated via softwood cuttings in Monterey County, Calif. in August of 2011.

'DrisBlueTwentyFive' was subsequently asexually propagated via softwood cuttings and tissue culture and underwent further testing in Linn County, Oreg. for 6 years (2014 to 2019). The present blueberry variety has been found to be stable and reproduce true to type through successive asexual propagations via softwood cuttings and tissue culture.

'DrisBlueTwentyFive' was selected for its sweet flavor, large fruit size, improved post-harvest storage qualities, and early ripening.

BRIEF DESCRIPTION OF THE DRAWINGS

This new blueberry plant variety is illustrated by the accompanying photographs. The colors shown are as true as can be reasonably obtained by conventional photographic procedures. The photographs are of plants that are five years old, unless otherwise specified.

DETAILED BOTANICAL DESCRIPTION

Figure 1:
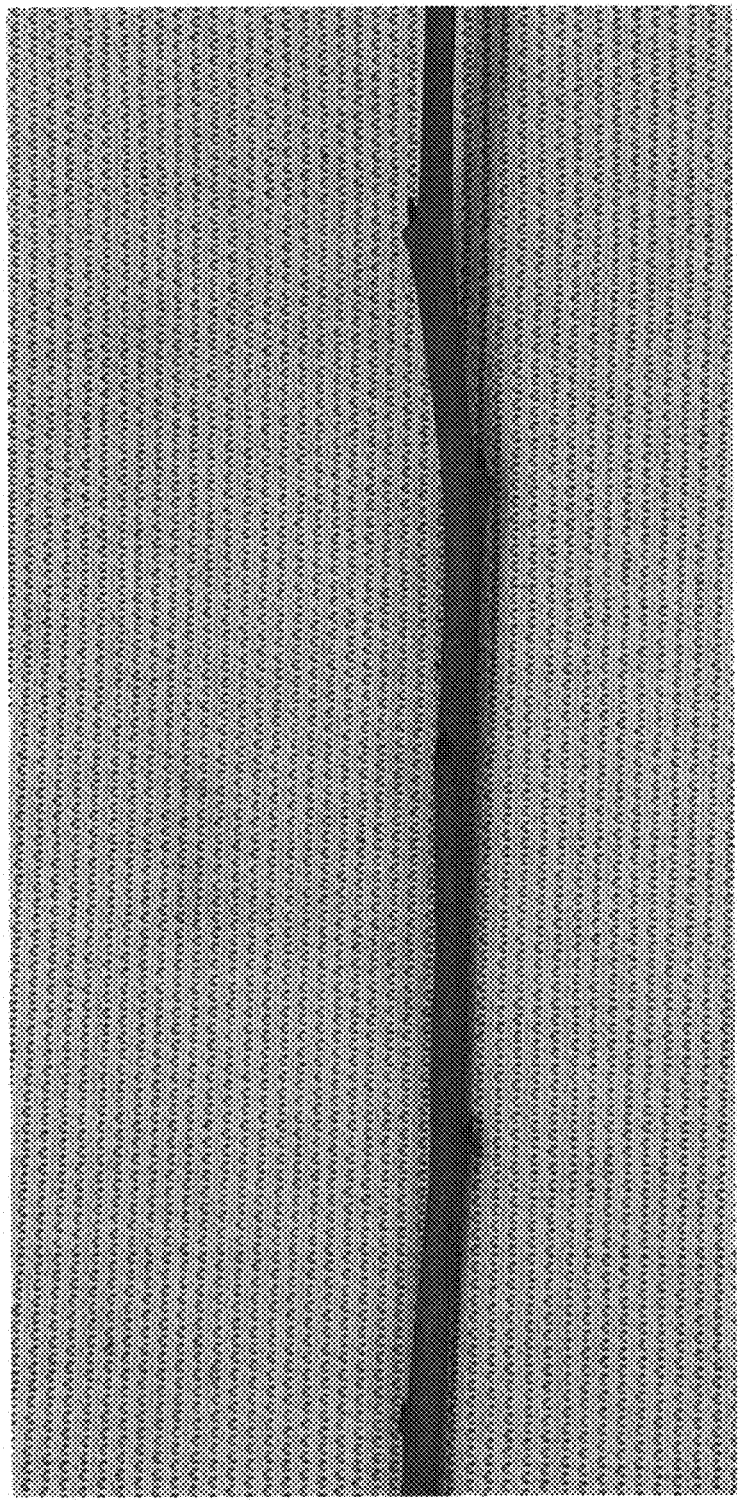
FIG. 1 illustrates a section of a cane of variety 'DrisBlueTwentyFive'.
Figure 2:
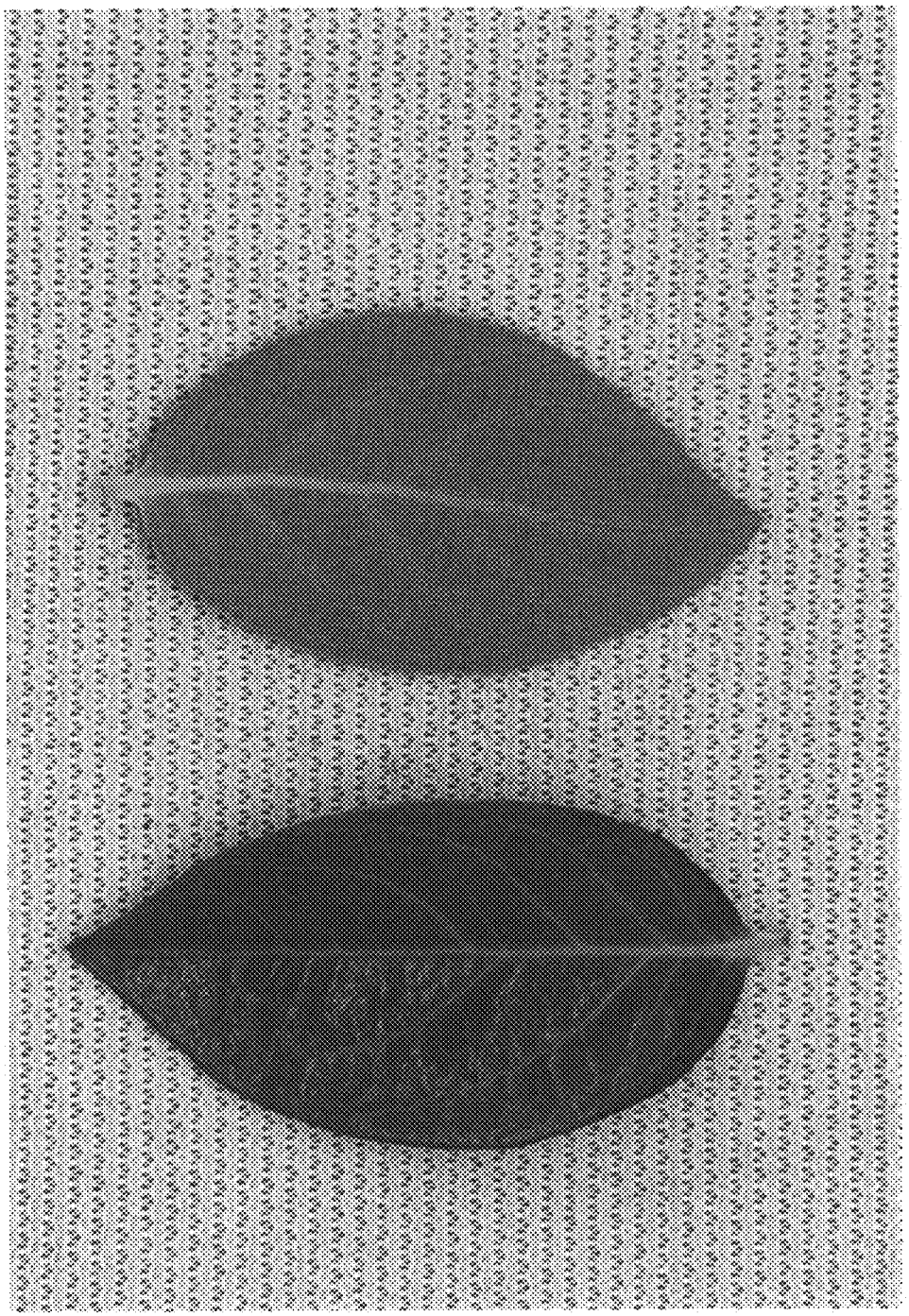
FIG. 2 illustrates leaves of variety 'DrisBlueTwentyFive'. The leaf on the left shows the upper leaf surface and the leaf on the right shows the lower leaf surface.
Figure 3:
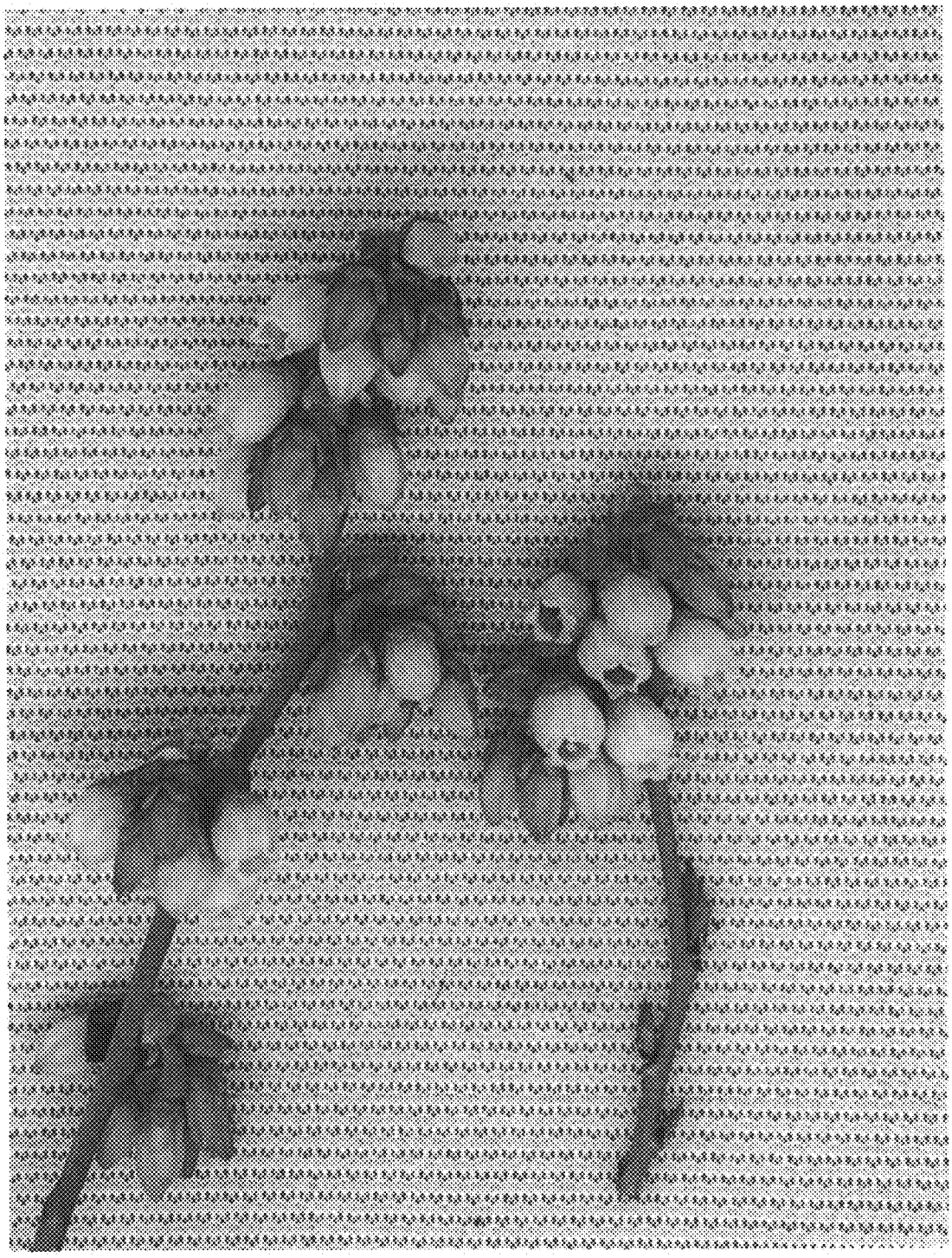
FIG. 3 illustrates clusters of flowers of variety 'DrisBlueTwentyFive'.
Figure 4:
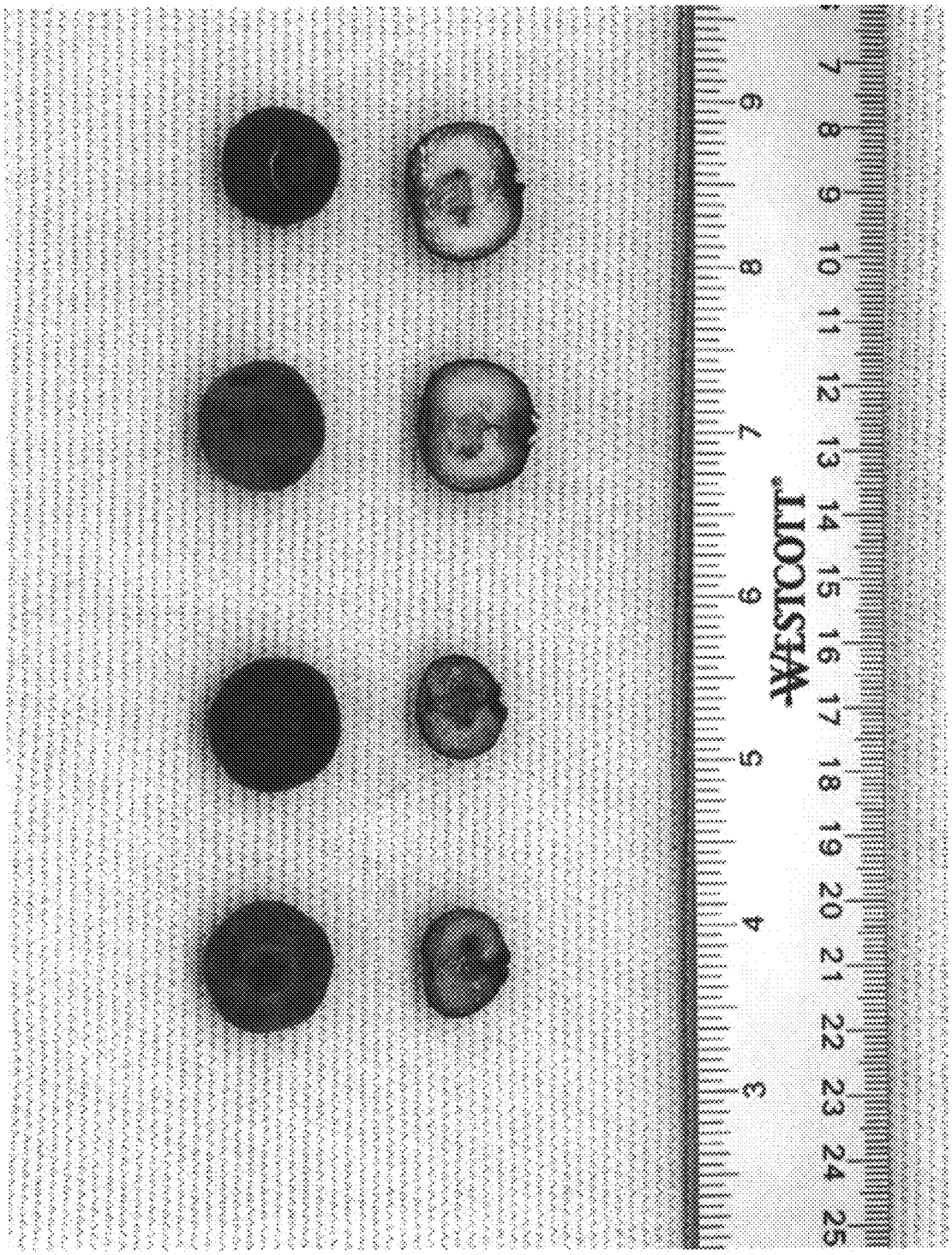
FIG. 4 illustrates whole fruits (top row) and longitudinal sections (bottom row) of variety 'DrisBlueTwentyFive'. The two fruits on the top left show the top view (calyx basin) of the whole fruit, whereas the two fruits on the top right show the bottom view (fruit-pedicel junction) of the whole fruit. The first and third fruit of the top row have bloom on them, whereas the second and fourth fruit of the top row have bloom removed.
Figure 5:
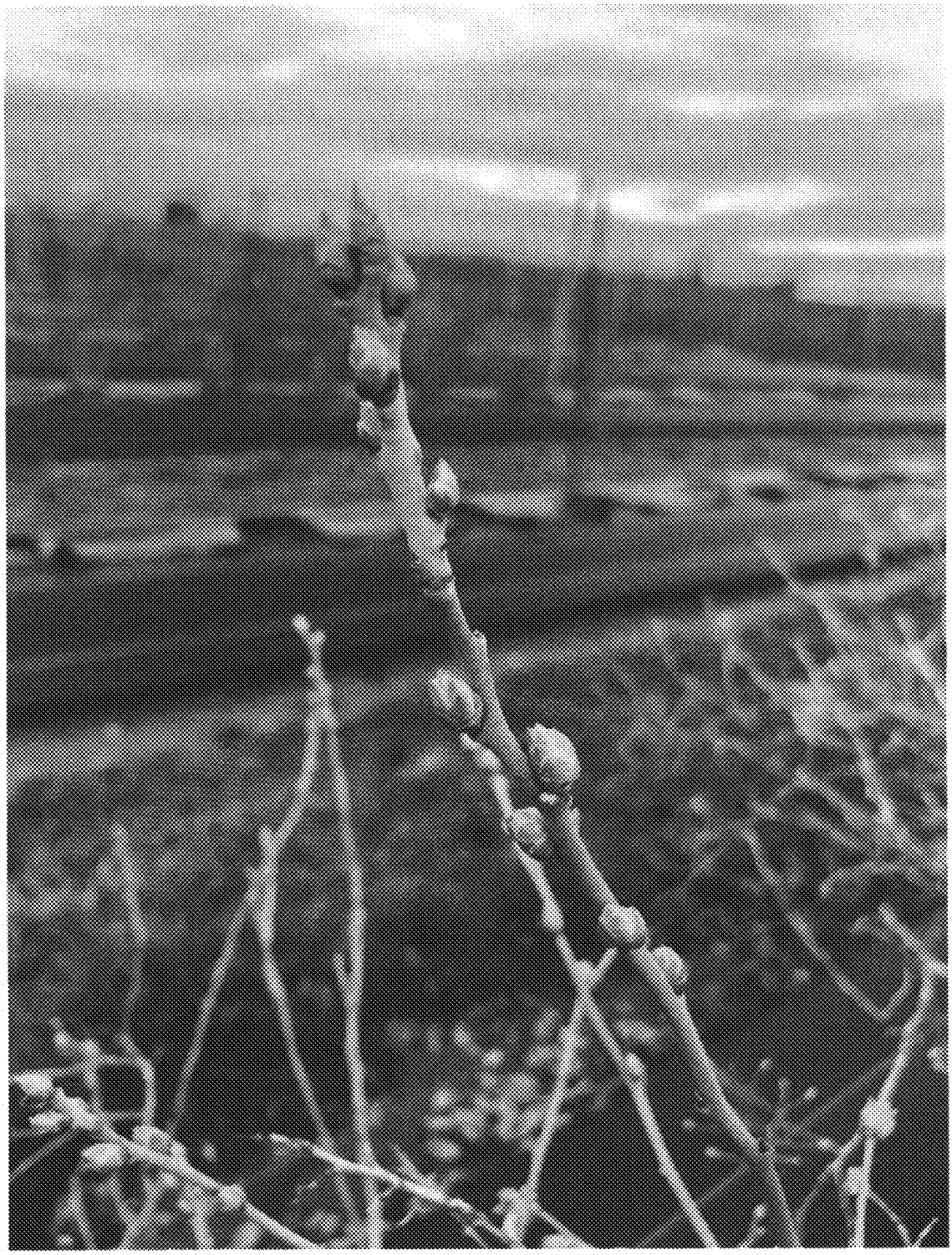
FIG. 5 illustrates buds on plants of variety 'DrisBlueTwentyFive'.
Figure 6:
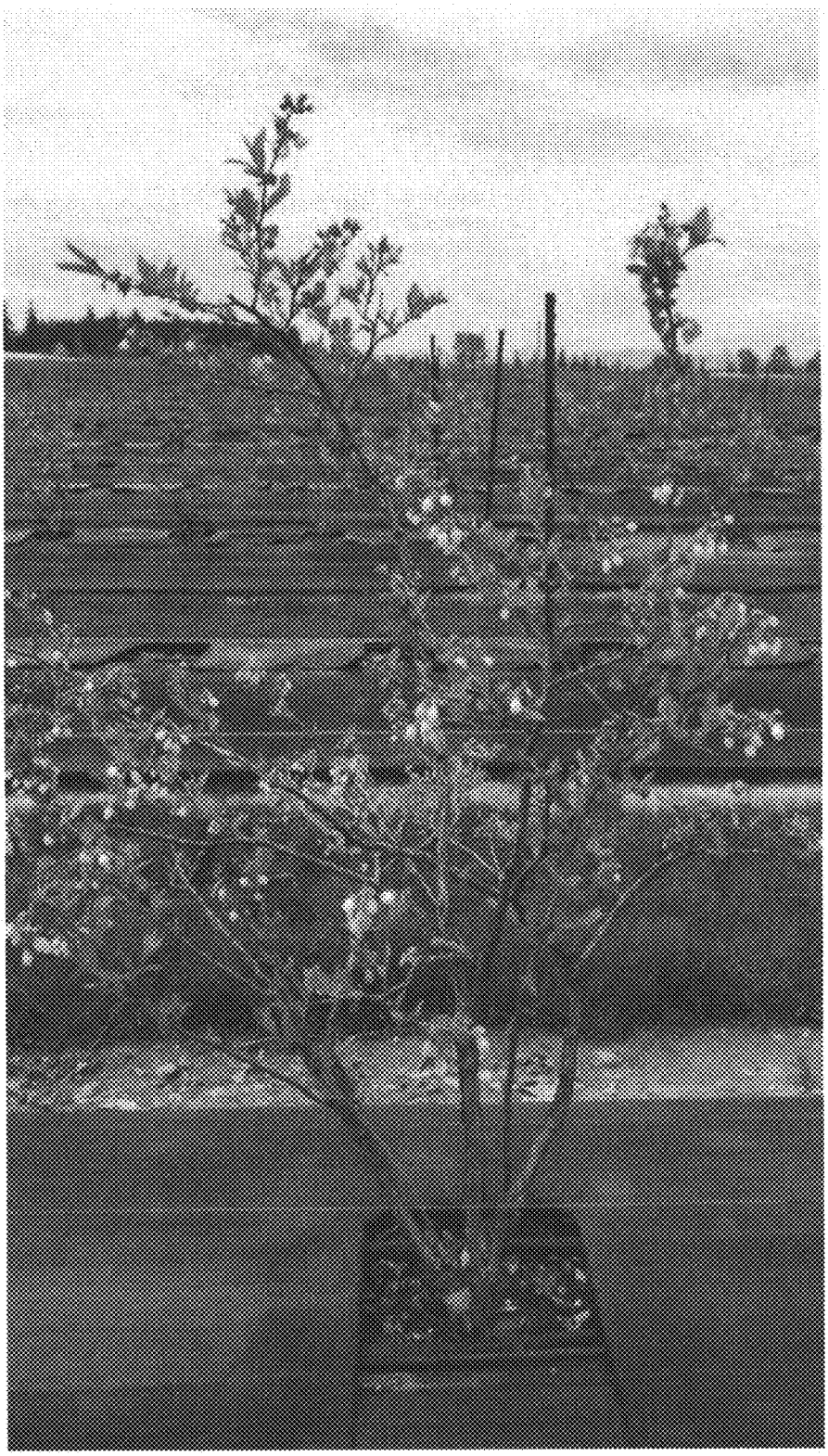
FIG. 6 illustrates flowering plants of variety 'DrisBlueTwentyFive'.
Figure 7:
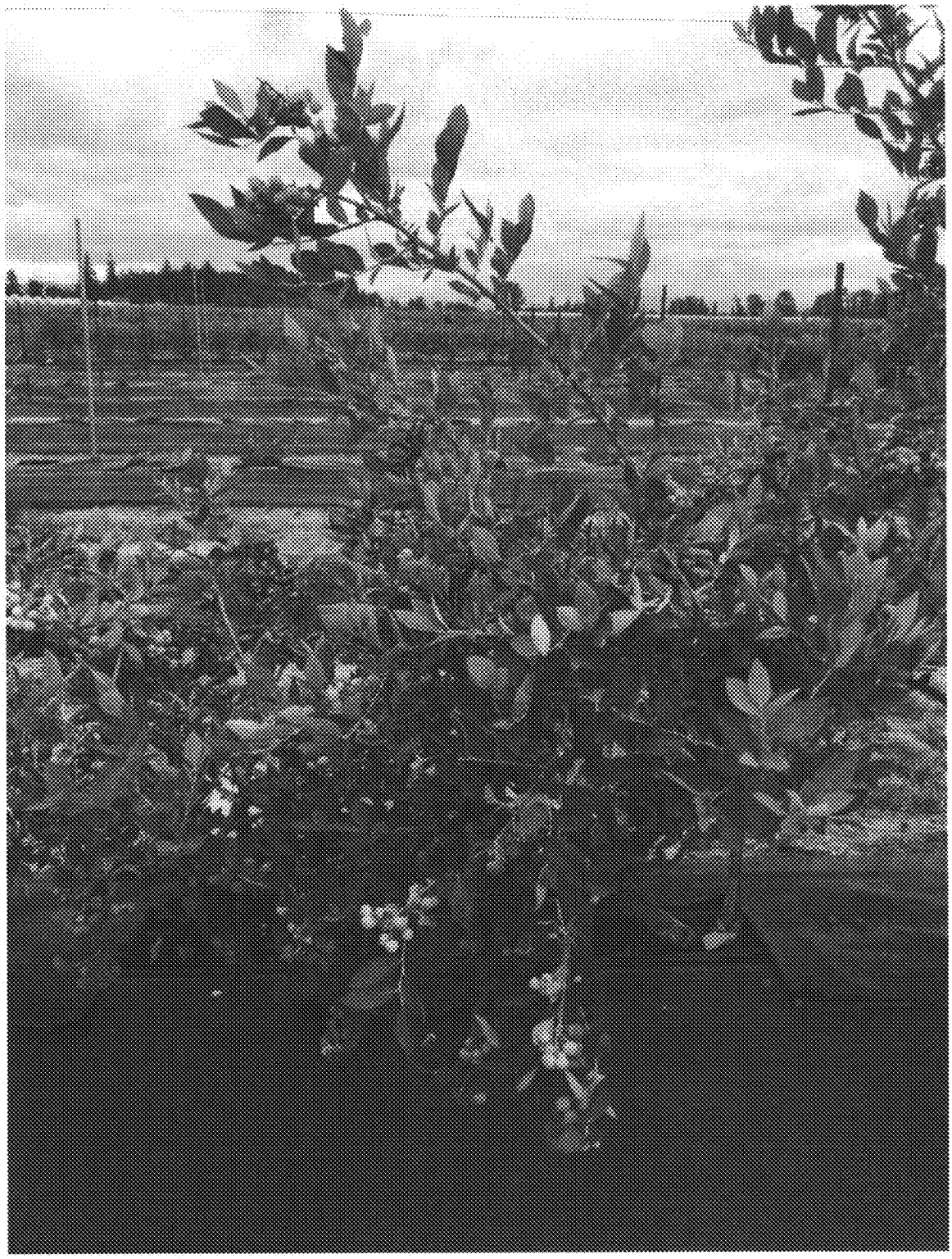
FIG. 7 illustrates fruiting plants of variety 'DrisBlueTwentyFive'.

The following description sets forth the distinctive characteristics of 'DrisBlueTwentyFive'. The data which define these characteristics is based on observations taken in Linn County, Oreg. from 2014 to 2019. This description is in accordance with UPOV terminology. Color designations, color descriptions, and other phenotypical descriptions may deviate from the stated values and descriptions depending upon variation in environmental, seasonal, climatic and cultural conditions. 'DrisBlueTwentyFive' has not been observed under all possible environmental conditions. Unless noted otherwise, the botanical description of 'DrisBlueTwentyFive' was taken from plants that were five years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family.*—Ericaceae.

*Botanical.*—*Vaccinium corymbosum* L.

*Common name.*—Blueberry.

*Variety name.*—'DrisBlueTwentyFive'.

Parentage:

*Female parent.*—The proprietary blueberry plant '90E 2' (unpatented).

*Male parent.*—The proprietary blueberry plant '10E 1' (unpatented).

Plant:

*Height.*—102.9 cm.

*Width.*—102.2 cm.

*Length/width ratio.*—1.0.

*Vigor.*—Medium.

*Growth habit.*—Upright.

*Chilling requirements.*—Minimum of 700 hours of chilling below 7° C. for proper vegetative and floral bud break.

*One-year-old canes* (*young canes*).—Length: 10 cm. Diameter at the base: 2 mm. Diameter at the tip: 1 mm. Internode length on the upper half: 15.5 mm. Color: RHS 153D (Strong yellow).

*Five-year-old canes* (*mature canes*).—Length: 62 cm. Diameter at the base: 17 mm. Diameter at the tip: 7 mm. Surface texture: Rough. Color: RHS 199C (Light yellowish brown).

Leaves:

*Length.*—72.0 mm.

*Width.*—32.9 mm.

*Length/width ratio.*—2.2.

*Shape.*—Ovate.

*Margin.*—Entire.

*Color on upper side.*—RHS 147A (Moderate olive green).

*Color of lower side.*—RHS 191B (Greyish yellow-green).

*Leaf apex shape.*—Acute.

*Leaf base shape.*—Cuneate.

*Petiole.*—Length: 3.5 mm. Diameter: 1.69 mm.

Flowers:

*Inflorescence density.*—Dense.

*Flower length* (*excluding peduncle*).—11.91 mm.

*Flower diameter.*—7.01 mm.

*Flower length/width ratio.*—1.7.

*Flower bud.*—Length: 8.61 mm. Width: 4.19 mm. Number of flowers per bud: 8. Color with anthocyanin present: RHS N 57A (Vivid purplish red).

*Flower pedicel.*—Length: 7.41 mm. Diameter: 1.26 mm.

*Corolla.*—Shape: Urceolate. Anthocyanin coloration on corolla tube: Weak. Color of corolla tube (with anthocyanin present): RHS 154D (Light yellow green). Ridges on corolla tube: Present. Conspicuousness of corolla tube ridges: Weak. Petal width (ridge to ridge): 2.44 mm. Diameter of corolla aperture: 3.34 mm.

*Reproductive organs.*—Style length (including stigma): 8.20 mm.

*Time of beginning of flowering on one-year-old shoot.*—Late February.

*Flowering interval on one-year-old shoot.*—Late February to mid-May.

Fruit:

*Length.*—15.24 mm.

*Diameter.*—19.45 mm.

*Length/width ratio.*—0.8.

*Weight.*—1.9 grams.

*Shape in longitudinal section.*—Oblate.

*Attitude of sepals.*—Erect to semi-erect.

*Type of sepals.*—Incurving.

*Calyx.*—Length: 5.54 mm. Width: 5.54 mm. Surface texture: Smooth. Color: RHS 98D (Light purplish blue).

*Calyx basin.*—Diameter: 5.54 mm. Depth: 2.08 mm. Diameter/depth ratio: 2.7.

*Number of berries per cluster.*—6.30.

*Fruit cluster peduncle length.*—14.06 mm.

*Diameter of fruit pedicel.*—1.08 mm.

*Color of unripe fruit.*—RHS N 144A (Strong yellowish green).

*Intensity of bloom.*—Medium.

*Color of fruit without bloom on mature fruit.*—RHS 103A (Greyish purplish blue).

*Fruit flesh color.*—RHS 194C (Yellowish grey).

*Fruit firmness.*—Medium-soft to medium.

*Fruit sweetness.*—Medium.

*Fruit acidity.*—Low.

*Seed.*—Length: 1.70 mm. Width: 1.04 mm. Length/width ratio: 1.6.

*Fruiting type.*—On one-year-old shoots.

*Ripening interval on one-year-old shoot.*—Early March to late June.

*Yield.*—6,688 kg to 10,431 kg of fruit per hectare per season from 60-month old plants when grown at Albany, Oreg.

*Market use of fruit.*—Fresh market.

*Shipping quality and fruit storage life.*—Following harvest, fruit have been stored for 21 days under standard blueberry storage conditions.

Resistance to abiotic stress, pests, and diseases:

*Botrytis fruit rot* (*Botrytis cinerea*).—Susceptible.

*Blueberry shock virus.*—Resistant.

COMPARISONS TO PARENTAL AND REFERENCE BLUEBERRY VARIETIES

'DrisBlueTwentyFive' differs from the proprietary female parent '90E 2' (unpatented) in that 'DrisBlueTwentyFive' has a larger fruit size, sweeter flavor, and a higher chilling requirement compared to female parent '90E 2'.

'DrisBlueTwentyFive' differs from the proprietary male parent '10E 1' (unpatented) in that 'DrisBlueTwentyFive' has a larger fruit size, sweeter flavor, and lower firmness compared to male parent '10E 1'.

'DrisBlueTwentyFive' differs from the reference blueberry plant variety 'DrisBlueTen' (U.S. Plant Pat. No. 26,643) in that 'DrisBlueTwentyFive' has an upright growth habit, medium plant vigor, ovate leaf shape, and medium intensity of bloom on fruit, whereas 'DrisBlueTen' has a semi-upright to spreading growth habit, strong plant vigor, elliptic leaf shape, and strong intensity of bloom on fruit.

'DrisBlueTwentyFive' differs from the reference blueberry plant variety 'DrisBlueNine' (U.S. Plant Pat. No. 26,287) in that 'DrisBlueTwentyFive' has an upright growth habit, the time of beginning of fruit ripening on one-year-old shoot is very early, has an ovate leaf shape, and a medium intensity of bloom, whereas 'DrisBlueNine' has as semi-erect growth habit, the time of beginning of fruit ripening on one-year-old shoot is late, has an elliptic leaf shape, and strong intensity of bloom on fruit.

What is claimed is:

1. A new and distinct variety of blueberry plant designated 'DrisBlueTwentyFive' as shown and described herein.

* * * * *